United States Patent [19]
Chakrabarti

[11] 3,976,586
[45] Aug. 24, 1976

[54] MONOESTERS DERIVED FROM ETHOXYLATED HIGHER ALCOHOLS AND THIODISUCCINIC ACID AS DETERGENT BUILDERS

[75] Inventor: Paritosh M. Chakrabarti, Wayne, N.J.

[73] Assignee: GAF Corporation, New York, N.Y.

[22] Filed: Oct. 8, 1975

[21] Appl. No.: 620,590

[52] U.S. Cl.............................. 252/89 R; 252/549; 252/557; 252/558; 252/DIG. 11; 260/481 R
[51] Int. Cl.²................... C11D 1/06; C07C 149/20
[58] Field of Search............ 252/89, 549, 551, 554, 252/555, 557, 558, DIG. 11; 260/535, 481 R

[56] References Cited
UNITED STATES PATENTS

| | | | |
|---|---|---|---|
| 2,603,653 | 7/1952 | Kosmin | 260/481 |
| 2,603,654 | 7/1952 | Kosmin | 260/481 |
| 2,654,773 | 10/1953 | Zerbe | 260/470 |
| 3,635,830 | 1/1972 | Lamberti et al. | 252/89 X |
| 3,753,913 | 2/1973 | Jarowenko | 252/89 |
| 3,784,486 | 1/1974 | Nelson et al. | 252/546 |
| 3,912,663 | 10/1975 | Lamberti | 252/542 |

FOREIGN PATENTS OR APPLICATIONS

| | | |
|---|---|---|
| 2,136,360 | 2/1973 | Germany |
| 2,157,456 | 6/1972 | Germany |

OTHER PUBLICATIONS

Schwab et al., *J. Agr. Food Chem.*, 3,518–21, "Preparation and Evaluation of Two New Fat–Soluble Metal Inactivaters," C.A. 49:10547g.

*Primary Examiner*—P. E. Willis, Jr.
*Attorney, Agent, or Firm*—Walter C. Kehm; Joshua J. Ward

[57] ABSTRACT

New monoesters derived from ethoxylated higher alcohols and thiodisuccinic acid having the formula:

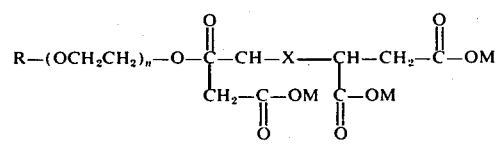

in which R is a hydrocarbon having from 12 to 22 carbon atoms, X is sulfur, sulfinyl, or sulfonyl, M is hydrogen, a monovalent metal, ammonium or a salt of ammonium, and $n$ is an integer ranging from 2 to 15, are useful as detergent builders and are particularly suitable for hard water detergents. In preferred esters, R is alkyl or alkenyl, X is sulfur, M is hydrogen or sodium, and $n$ is an integer ranging from 3 to 7.

15 Claims, No Drawings

MONOESTERS DERIVED FROM ETHOXYLATED HIGHER ALCOHOLS AND THIODISUCCINIC ACID AS DETERGENT BUILDERS

This invention relates to monoesters derived from ethoxylated higher alcohols. More particularly, this invention relates to said monoesters and their use as detergent builders in improved detergent compositions.

It is known that some materials improve the detergency levels of soaps and synthetic detergents nd these are commonly used in detergent compositions. Such cleaning boosters are called "builders". "Builders" permit the attainment of superior cleaning performance, both as regards cost and quality of finished work, than is possible when so-called unbuilt compositions are used.

The behavior and mechanism by which builders perform their function is not fully understood although several explanations for their behavior are available. Unfortunately, an unequivocal criterion does not exist which would permit one to predict accurately which class of compounds possess valuable builder properties and which compounds do not.

This may be explained in part by the complex nature of detergency and the countless factors which contribute to overall performance results. Builder compounds have been found to have some effect, for instance, in such areas as stabilization of solid soil suspensions, emulsification of soil particles, solubilization of water-insoluble materials, foaming of washing solutions, peptization of soil agglomerates, neutralization of acid soil, and the inactivation of mineral constituents present in the washing solution. Thus, any theoretical discussion of the detergent boosting capacity of a builder compound must take into account all the significant individual actions involved in the detergent process and all usual conditions of soiling and washing.

Examples of known inorganic builder materials include: water-soluble inorganic alkaline builder salts which can be used alone or in combination, including alkali metal carbonates, borates, phosphates, polyphosphates, bicarbonates and silicates.

Examples of known organic builder materials include: alkali metal, ammonium or substituted ammonium aminopolycarboxylates, e.g. sodium and potassium ethylenediaminetetraacetate, sodium and potassium triethanolammonium-N-(2-hydroxyethyl)-nitrilotriacetate. Alkali metal salts of phytic acid, e.g. sodium phytate, are also suitable as organic builders.

In recent years owing, in large measure, to governmental pressure against the use of detergent builders containing phosphorus and/or nitrogen, there has been great activity directed toward the development of detergent builders not containing these elements. A wide variety of long-chain compounds have been, and still are being, investigated for possible use as detergent builders; these include, but are not limmited to, various starches, polyelectrolytes and water soluble salts of carboxylic acid. For example, U.S. Pat. No. 3,308,067 discloses the use of various polyelectrolytes as detergent builders. British Pat. No. 1,293,753 indicates that certain water soluble salts of dicarboxylic acids can be employed as detergent builders. Many of these new builders are not suitable for commercial use, either because of excessively high cost when compared to currently available phosphorus and nitrogen-containing builders or even when compared to builders not containing these elements, or because of unstisfactory performance in detergent compositions such as, for example, ineffectiveness in hard water, undesirable buildup on fabrics, etc.

It is therefore a prime object of this invention to develop a detergent builder, not containing phosphorus or nitrogen, which is economically attractive and avoids the foregoing disadvantages. Other objects will become apparent from the following disclosure.

SUMMARY OF THE INVENTION

Compounds having the structure

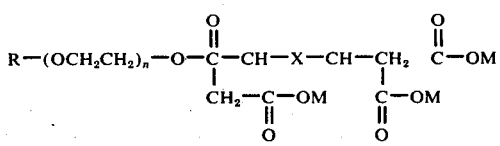

in which R is a hydrocarbon having from 12 to 22 carbon atoms, X is sulfur, sulfinyl, or sulfonyl, each M (which may be the same or different) is hyrogen, a monovalent metal, ammonium, substituted ammonium,, or a salt of ammonium, and $n$ is an integer ranging from 2 to 15, are useful as detergent builders and are particularly suitable for heavy-duty detergents and hard water detergents. Use of these builders does not lead to undesirable buildup on fabrics. These compounds are new compounds derived from ethoxylated higher alcohols and thiodisuccinic acid. Preferred compounds are those in which R is alkyl or alkenyl, M is hydrogen or sodium, X is sulfur and $n$ is an integer ranging from 3 to 7.

DETAILED DISCLOSURE

The compounds of this invention, which are new compounds, are water soluble salts of monoesters of thiodisuccinic acid with ethoxylated alcohol. These salts are white solids, readily soluble in water, do not form undesirable precipitates with hard water and do not lead to their buildup on fabrics.

In the above-indicated formula R is preferably an alkyl or alkenyl group having from 12 to 22 carbon atoms, preferably a straight chain alkyl or alkenyl. S is preferably sulfur. The monovalent metals in the definition of M include the alkali metals such as lithium, sodium and potassium, preferably sodium. By "substituted ammonium" is meant ammonium substituted by alkyl or hydroxyalkyl having from 1 to 4 carbon atoms, such as methyl, ethyl, n-propyl, isopropyl, hydroxyethyl or hydroxypropyl. The integer symbol $n$ preferably stands for a number ranging from 3 to 7.

The compounds of this invention in which X is sulfur are prepared by reacting the ethoxylated alcohol with a stoichiometric amount of maleic anhydride. The resulting adduct, which is a half ester of maleic acid, is then reacted with thiomalic acid in the presence of an alkali such as sodium hyroxide.

Compounds in which X is sulfur can be readily oxidized to the corresponding sulfoxides and sulfones by methods well known in the art such as, for example, oxidation by hydrogen peroxide, nitric acid, permanganate, bromine, etc.

In general, in the detergent compositions of this invention, the essential ingredients are (a) an organic water soluble detergent surface active material as defined and illustrated below and (b) the monoester builder compound meeting the requirements specified and exemplified herein.

The detergent compositions of this invention contain the essential ingredients in a ratio of monoester builder to detergent surfactant in the range of about 1:5 to about 10:1 by weight, with such compositions providing in aqueous solution a pH of from about 7 to about 12. The preferred ratio of builder to detergent surfactant is about 1:2 to about 5:1 and the optimum pH range is 7.5 to about 11:5.

The detergent surface active compounds which can be used within the compositions of this invention include anionic, nonionic, zwitterionic, ampholytic detergent compounds and mixtures thereof. These suitable substances are outlined at length below:

a. Anionic detergent compositions which can be used in the compositions of this invention include both soap and non-soap detergent compounds. Examples of suitable soaps are the sodium, potassium, ammonium and alkylolammonium salts of higher fatty acids ($C_{10}$–$C_{20}$). Particularly useful are the sodium or potassium salts of the mixtures of fatty acids derived from coconut oil and tallow, i.e., sodium of potassium tallow and coconut soap, tall oils and SAS (sodium alkane sulfonates). Examples of anionic organic non-soap detergent compounds are the water soluble alkali metal salts of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the synthetic detergents which form a part of the compositions of the present invention are the sodium or potassium alkyl sulfates especially those obtained by sulfating the higher alcohols ($C_8$–$C_{18}$ carbon atoms) produced by reducing the glycerides of tallow or coconut oil: sodium or potassium alkyl benzenesulfonates, such as are described in U.S. Pat. Nos. 2,220,009 and 2,477,383 in which the alkyl group contains from about 9 to about 15 carbon atoms; other examples of alkali metal alkylbenzene sulfonates are those in which the alkyl radical is a straight or branched chain aliphatic radical containing from about 10 to about 20 carbon atoms for instance, in the straight chain variety 2-phenyl-dodecansulfonate and 3-phenyl-dodecane-sulfonate; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g. tallow or coconut oil alcohols) and about 1 to 6 moles of ethylene oxide; sodium or potassium salts or alkylphenol ethylene oxide ether sulfate with about 1 to about 10 units of ethylene oxide per molecule and in which the alkyl radicals contain about 9 to about 12 carbon atoms; the reaction product of fatty acids esterfied with isethionic acid and neutralized with sodium hydroxide where, for example, the fatty acids are derived from coconut oil; sodium or potassium salts of fatty acid amide of a methyl tauride in which the fatty acids, for example, are derived from coconut oil; and others known in the art.

b. Nonionic synthetic detergents may be broadly defined as compounds aliphatic or alkylaromatic in nature which do not ionize in water solution. For example, a well-known class of nonionic synthetic detergents is made available on the market under the trademark "Pluronic". These compounds are formed by condensing ethylene oxide with an hydrophobic base formed by condensing ethylene oxide with an hydrophobic base formed by the condensation of propylene oxide with propylene glycol. The hydrophobic portion of the molecule which, of course, exhibits water insolubility, has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product.

Other suitable nonionic synthetic detergents include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octene, or nonene, for example.

2. Those derived from the condensation of ethylene oxide with the product resulting from the reaction of propylene oxide and ethylene diamine. For example, compounds containing from about 40 to about 80% polyoxyethylene by weight and having a molecular weight of from about 5,000 to 11,000 resulting from the reaction of ethylene oxide groups with a hydrophobic base constituted of the reaction product of ethylene diamine and excess propylene oxide, said hydrophobic bases having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol-ethylene oxide per mole of coconut alcohol, the coconut alcohol fraction having from 10 to 14 carbon atoms.

4. Long chain tertiary amine oxides corresponding to the following general formula, $R_1R_2R_3N \rightarrow O$, wherein $R_1$ is an alkyl radical of from about 8 to 18 carbon atoms, and $R_2$ and $R_3$ are each methyl or ethyl radicals. The arrow in the formula is a conventional representation of a semipolar bond. Examples of amine oxides suitable for use in this invention include dimethyldodecylamine oxide, dimethyloctylamine oxide, dimethyldecylamine oxide, dimethyltetradecylamine oxide, dimethylhexadecylamine oxide.

Long chain tertiary phosphine oxides corresponding to the following formula $RR'R''P \rightarrow O$, wherein R is an alkyl, alkenyl or monohydroxyalkyl radical ranging from 10 to 18 carbon atoms in chain length and R' and R'' are each alkyl or monohydroxyalkyl groups containing from 1 to 3 carbon atoms. The arrow in the formula is a conventional representation of a semipolar bond. Examples of suitable phosphine oxide are:

dimethyldodecylphosphine oxide,
dimethyltetradecylphosphine oxide,
ethylmethyltetradecylphosphine oxide,
cetyldimethylphosphine oxide,
dimethylstearylphosphine oxide,
cetylethylpropylphosphine oxide,
diethyldodecylphosphine oxide, diethyltetradecylphosphine oxide,
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide, 6. Dialkyl sulfoxides corresponding to the following formula, $RR'S \rightarrow O$, wherein R is an alkyl, alkenyl, beta or gamma-monohydroxyalkyl radical or an alkyl or beta or gamma-monohydroxyalkyl radical containing one or two oxygen atoms in the chain, the R groups ranging from 10 to 18 carbon atoms in chain length, and wherein R is methyl or ethyl. Examples of suitable sulfoxide compounds are:

dodecylmethylsulfoxide
tetradecylmethylsulfoxide
3-hydroxytridecylmethylsulfoxide
2-hydroxydodecylmethylsulfoxide
3-hydroxy-4-decybutylmethylsulfoxide
3-hydroxy-4-dodecoxybutylmethylsulfoxide
2-hydroxy-3-decoxypropylmethylsulfoxide
2-hydroxy-3-dodecoxypropylmethylsulfoxide
dodecyl ethyl sulfoxide
2-hydroxydodecylethylsulfoxide The 3-hydroxy-4-decoxybutyl methyl sulfoxide has been found to be an especially effective detergent surfactant.

c. Ampholytic synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group. Examples of compounds falling within this definition are sodiun-3-dodecylaminopropionate and sodium-3-dodecylaminopropanesulfonate.

d. Zwitterionic synthetic detergent surfactants can be broadly described as derivatives of aliphatic quaternary ammonium compounds in which the aliphatic radical may be straight or branched and wherein one of the aliphatic substituents contains from about 8 to 18 carbon atoms and one contains an anionic water solubilizing group. Examples of compounds falling within this definition are 3-(N,N-dimethyl-N-hexadecylammonio)-2-hydroxypropane-1-sulfonate which are especially preferred for their excellent cool water detergency characteristics.

The anionic, nonionic, ampholytic and zwitterionic detergent surfactants mentioned above can be used singly or in combination in the practice of the present invention. The above examples are merely specific illustrations of the numerous detergents which can find application within the scope of this invention.

A granular detergent composition can contain a monoester builder of this invention and a detergent surfactant in the weight ratio of about 1:1.5 to about 10:1. The preferred ratio of builder to surfactant is about 1:2 to about 5:1. Another embodiment of this invention is a built liquid detergent composition containing a builder described above and a detergent surfactant in a weight ratio of builder to detergent of about 1:1.5 to about 10:1. The preferred ratio for build liquid compositions of built to detergent is about 1:2 to about 3:1.

In a finished detergent formulation of this invention there will often be added in minor amounts materials which make the product more effective or more attractive. The following are mentioned by way of example.

Soluble sodium carboxymethylcellulose (CMC) can be added in minor amounts to inhibit soil redeposition. A tarnish inhibitor such as ethylenethiourea can also be added in amounts up to about 2%. An alkaline material or alkali such as sodium hydroxide or potassium hydroxide can be added in minor amounts as supplementary pH adjusters. There might also be mentioned as suitable additives, water, brightening agents, bleaching agents, sodium sulfate, and sodium carbonate. Corrosion inhibitors can be added. Soluble silicates are highly effective inhibitors and can be added to formulations within this invention at levels of from about 3% to about 8%. Alkali metal, preferably potassium or sodium, silicates having a weight ratio of $SiO_2:Y_2O$ of from 1:1 to 2.8:1 can be used. Y in this ratio refers to sodium or potassium. A sodium silicate having a ratio of $SiO_2:Na_2O$ of about 1.6:1 to 2.45:1 is especially preferred for economy and effectiveness.

The invention will be better understood by reference to the following examples, which are included here for illustrative purposes only and are not intended as limitations. Unless otherwise stated, all percentages and parts are by weight.

EXAMPLE 1

Preparation of trisodium salt of thiodisuccinic acid monoesterified with an ethoxylated $C_{12}$–$C_{15}$ alcohol, 3 moles of ethoxylene oxide (Neodol 25-3, Shell).

A mixture of Neodol 25-3 (33.9 g. = 0.1 mole) and maleic anhydride (9.8 g. = 0.1 mole) was heated at 80°C. for 3 hours. The resulting half ester was treated with a solution of sodium hydroxide (4 g.) in water (150 ml.), when a thick viscous paste resulted. This was treated with a solution of disodium thiomalate prepared by dissolving thiomalic acid (15 g. = 0.1 mole) in aqueous sodium hydroxide (8 g. in 200 ml. water) and the mixture stirred at 55°C. for 3 hours, during which a clear less viscous solution resulted. The solution was then poured into acetone (600 ml.) and the precipitated white solid, the trisodium salt of Neodol 25-3 ($C_{12}$–$C_{15}$ alcohol + 3 E. O.) monoester of thiodisuccinic acid, was filtered, washed with fresh acetone and dried under vacuum at 60°C. for 1 hour. (Compound No. 1)

Similarly prepared were the trisodium salts of thiodisuccinic acid, monoesterified with an ethoxylated $C_{12}$–$C_{15}$ alcohol, 7 moles of ethylene oxide (Neodol 25-7, Shell), and with an ethoxylated $C_{12}$–$C_{15}$ alcohol, 9 moles of ethylene oxide (Neodol 25-9, Shell). These salts are designated as Compound No. 2 and Compound No. 3, respectively.

EXAMPLES 2–5

These examples show detergency test results of formulations containing the compounds of this invention with those containing sodium tripolyphosphate as builder.

Detergency tests were carried out in terg-o-tometers using the following conditions:

Water: 150 ppm hard ($Ca^{++}:Mg^{++}$ = 60:40), liter/beaker
Temperature: 49°C.
Agitation: 110 rpm
Wash Cycle: 10 minutes
Rinse Cycle: 5 minutes (one rinse)
Detergent Concentration: 1.5 g./1000 ml. water
Fabric load/beaker (soiled):
 2–10 cm. × 12.7 cm. cotton without finish 2–10 cm. × 12.7 cm. dacron/cotton (65:35) without permanent press finish 2–10 cm. × 12.7 cm. dacron/cotton (65:35) with permanent press finish 2–10 cm. × 12.7 cm. spun nylon The fabrics were standard soiled fabrics from Test Fabrics Inc.

Reflectances of the swatches were measured in unsoiled regions, in soiled regions before washing and in the soiled regions after washing, using a Hunter Reflectometer. Results were expressed as percent soil removed (SR) according to the following equation:

$$\% \ SR = \frac{R_w - R_s}{R_o - R_s} \cdot 100$$

where $R_o$ = reflectance of unsoiled cloth
$R_s$ = reflectance of soiled cloth before washing
$R_w$ = reflectance of soiled cloth after washing Table I

| | Products Tested | | | |
|---|---|---|---|---|
| | | Product | | |
| Ingredients | A | B | C | D |
| Sodium Dodecylbenzene Sulfonate (act.) | 20.0% | 20.0% | 20.0% | 20.0% |
| Na$_2$SiO$_3$ . 5H$_2$O | 12.0 | 12.0 | 12.0 | 12.0 |
| Na$_2$SO$_4$ | 18.0 | 18.0 | 18.0 | 18.0 |
| STPP | 35.0 | — | — | — |
| Compound No. 1 | — | 50.0 | — | — |
| Compound No. 2 | — | — | 50.0 | — |
| Compound No. 3 | — | — | — | 50.0 |
| Water | 15.0 | — | — | — |

Results of terg-o-tometer detergency test using soil swatches from Test Fabrics Inc. are shown in Table II.

Table II

| | Terg-o-tometer Detergency Test (Soiled Fabric from Test Fabrics Inc.) | | | |
|---|---|---|---|---|
| | Product | % Soil Removed[1,2] | | |
| Example | (Table I) | Cotton | D/C-F | M | N |
| 2 | A | 37 | 29 | 28 | 44 |
| 3 | B | 36 | 36 | 37 | 37 |
| 4 | C | 36 | 35 | 36 | 49 |
| 5 | D | 34 | 32 | 34 | 40 |

[1]Average of 3 tests
[2]D/C-F = Dacron-cotton (65/35) with permanent press finish
M = Dacron-cotton (65/35) without permanent press finish
N = Spun nylon The above examples show that the compounds of this invention are effective detergent builders. Note that comparisons were made of these builders at 50% level with a 35% STPP built formulation (Product A).

EXAMPLES 6–12

Examples 2–5 showed preliminary detergency data using standard soiled fabrics from Test Fabrics Inc. Such soil however is not representative of natural soil. Further detergency tests were therefore carried out using simulated natural soil.

Swatches were soiled with simulated natural soil as described by Spangler et al, in *Journal of the American Oil Chemists Society*, 42, 723 (1965). The detergency test procedures were the same as those described under Examples 2–5.

Table III

| | Products Tested | | | | | | |
|---|---|---|---|---|---|---|---|
| | | | | Product | | | |
| Ingredients | A | B | C | D | E | F | G |
| Sodium dodecylbenzene sulfonate (act.) | 20% | 20% | 20% | 20% | — | 20% | 20% |
| Na$_2$SiO$_3$ . 5H$_2$O | 12 | 12 | 12 | 12 | 12% | 12 | 12 |
| Na$_2$SO$_4$ | 18 | 18 | 18 | 18 | 18 | 18 | 18 |
| STPP | 35 | — | — | — | — | — | — |
| Compound No. 1 | — | 50 | — | — | 50 | — | — |
| Compound No. 2 | — | — | 50 | — | — | — | — |
| Compound No. 3 | — | — | — | 50 | — | — | — |
| Sodium Citrate | — | — | — | — | — | 50 | — |
| Water | 15 | — | — | — | 20 | — | 50 |

Results of terg-o-tometer degergency test using swatches soiled by Spangler's simulated natural soil are shown in Table IV.

Table IV

| | Terg-o-tometer Detergency Test (Spangler's Simulated Natural Soil) | | | |
|---|---|---|---|---|
| | Product | % Soil Removed[1,2] | | |
| Example No. | (Table III) | Cotton | D/C-F | M | N |
| 6 | A | 43 | 10 | 45 | 55 |
| 7 | B | 46 | 25 | 52 | 63 |
| 8 | C | 46 | 15 | 45 | 56 |
| 9 | D | 45 | 15 | 39 | 52 |
| 10 | E | 42 | 15 | 36 | 42 |
| 11 | F | 30 | 18 | 18 | 21 |
| 12 | G | 16 | 20 | 12 | 8 |

[1]Average of 3 tests
[2]D/C-F = Dacron-cotton (65/35) with permanent press finish
M = Dacron-cotton (65/35) without permanent press finish
N = Spun nylon These results show that the compounds of this invention (Examples 7, 8 and 9) are excellent detergent builders when used in combination with sodium dodecylbenzene sulfonate and in this respect they are equivalent to or better than STPP (Example 6) and far superior to sodium citrate (Example 11).

Example 10 shows that the compositions of this invention are also excellent detergents in hard water and do not need to be built with STPP.

EXAMPLES 13–17

These examples illustrate superior properties of the compounds of this invention insofar as their tendency not to accumulate on the fabric is concerned.

Accumulation of mineral constituents of hard water on fabric caused by precipitation of insoluble interaction products of detergent components and Ca$^{++}$/Mg$^{++}$ ions usually lead to undesirable effects such as harsh feel, loss of flame retardancy in case of flame-retardant treated fabric, gradual yellowing and greying of fabric, etc.

Accumulation of mineral-detergent component interaction products on the fabric was studied by washing desized Indianhead cotton swatches (Test Fabric No. S 405) with experimental detergents according to a procedure which was a slight modification of that prescribed in AATCC Test Method 76–1968. According to the current procedure, four 10cm. × 12–7cm. cotton swatches were washed 10 times in terg-o-tometer beakers using the experimental detergent formulation. Each wash consisted of a 10 minute wash cycle at 49°C. and 110 strokes per minute with 1 liter of 150 ppm. hard (Ca:Mg = 60:40) water and 1.5 g. of the detergent formulation to be studied followed by a 5 minute rinse with 1 liter hard water at the same temperature and agitation; the swatches were removed from the beaker and hand wrung in between wash and rinse cycles. After each complete wash, the swatches were dried in an automatic clothes drier. After 10 such complete washes, the fabrics were cut into small pieces, dried at 100°C. until constant weight and then carefully charred in a crucible over a small flame and then ashed to constant weight at 800°C. Table VI shows percent ash content of the swatches after 10 complete washes using detergent formulations described in Table V.

Table V

| Ingredients | Products Tested | | | |
|---|---|---|---|---|
| | A | B | Product C | D |
| Sodium dodecylbenzene sulfonate (act.) | 20% | 20% | 20% | 20% |
| Na$_2$SiO$_3$ . 5H$_2$O | 12 | 12 | 12 | 12 |
| Na$_2$SO$_4$ | 18 | 18 | 18 | 18 |
| STPP | 35 | — | — | — |
| Compound No. 1 | — | 50 | — | — |
| Compound No. 2 | — | — | 50 | — |
| Compound No. 3 | — | — | — | 50 |
| Water | 15 | — | — | — |

Table VI

| Example No. | Ash Build-up Data Product Used (Table V) | % Ash After 10 Wash-Rinse Cycles |
|---|---|---|
| 13 | A | 0.18 |
| 14 | B | 0.25 |
| 15 | C | 0.17 |
| 16 | D | 0.15 |
| 17 | Control (without washing) | 0.22 |

As can be seen from the above examples, the compositions of this invention do not contribute to ash buildup.

EXAMPLES 18–20

The following examples show the calcium tolerance of the compounds of this invention.

Calcium tolerance was measured as follows: A standard solution (0.1 to 1M.) of Ca(NO$_3$)$_2$ was added dropwise (10 drops per minute) and with vigorous stirring to 100 ml. of 0.1% aqueous solution of the builder candidate. The volume at which first visible coagulation occured was noted. The results were expressed as g. Ca/100 g. candidate.

Table VII

| Example No. | Candidate | Ca-Tolerance in g./100 g.candidate |
|---|---|---|
| 18 | Compound No. 1 | 30 |
| 19 | Compound No. 2 | >600 |
| 20 | Compound No. 3 | >600 |

The results show that compositions of this invention have excellent tolerance towards hard water.

EXAMPLE 21

Compounds No. 1, No. 2 and No. 3 of Example 1 were oxidized to the corresponding sulfones as follows:

About 100 g. of Compound 1, 2 and 3 were each taken up in 500 ml. water and the solution treated with an aqueous solution containing 30% hydrogen peroxide until a slight excess of hydrogen peroxide persisted in the reaction medium (tested with acidified potassium iodide solution). The mixture was then agitated at 50° to 60°C. for 1 hour with addition of the 30% peroxide solution, if and when required, to keep a slight excess of peroxide during the reaction period. At the end of 1 hour, the mixture was poured into excess acetone (1 liter), the precipitated white solid filtered, washed with fresh acetone and dried under vacuum at 60°C. for 1 hour. The products derived from Compounds No. 1, No. 2 and No. 3 are the corresponding sulfones designated Compounds Nos. 4, 5 and 6, respectively, and had the following structures:

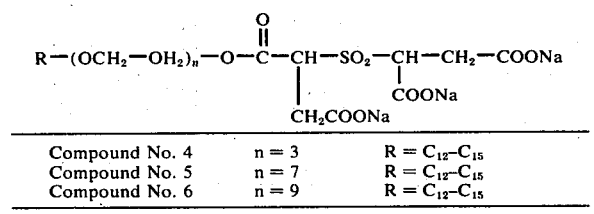

| | n | R |
|---|---|---|
| Compound No. 4 | n = 3 | R = C$_{12}$-C$_{15}$ |
| Compound No. 5 | n = 7 | R = C$_{12}$-C$_{15}$ |
| Compound No. 6 | n = 9 | R = C$_{12}$-C$_{15}$ |

Compounds Nos. 4, 5 and 6 are substantially equivalent to Compounds 1, 2 and 3 as builders for detergents and in controlling ash buildup.

EXAMPLE 22

A synthetic linear C$_{18}$ alcohol (available from Conoco Chemicals as Alfol 18 (C$_{18}$H$_{38}$O) and a tallow derived natural alcohol (available from the Proctor & Gamble Co., as TA 1618 alcohol), were ethoxylated using standard ethoxylation procedures to give the ethylene oxide adducts described in Table VIII.

TABLE VIII

| Adduct Designation | Structure | Average MW |
|---|---|---|
| TA 1618 + E.O. | R$^1$(OCH$_2$CH$_2$)$_2$—OH | 350 |
| TA 1618 + 10 E.O. | R$^1$(OCH$_2$CH$_2$)$_{10}$—OH | 702 |
| TA 1618 + 15 E.O. | R$^1$(OCH$_2$CH$_2$)$_{15}$—OH | 922 |
| Alfol 18 + 2 E.O. | C$_{18}$H$_{37}$(OCH$_2$CH$_2$)$_2$—OH | 357 |
| Alfol 18 + 10 E.O. | C$_{18}$H$_{37}$(OCH$_2$CH$_2$)$_{10}$—OH | 709 |
| Alfol 18 + 15 E.O. | C$_{18}$H$_{37}$(OCH$_2$CH$_2$)$_{15}$—OH | 929 |

[1]R is the composite alkyl radical of TA 1618 alcohol, which typically contains: 0.1% C$_{12}$, 3% C$_{14}$, 0.4% C$_{15}$, 27% C$_{16}$, 1.8% C$_{17}$, 65% C$_{18}$ and 1.1% C$_{20}$.

Trisodium salts of thiodisuccinic acid monoesterified with the ethoxylates described in Table VIII were prepared following the procedures described in Example 1. The resulting products are designated Compound No. 7, Compound No. 8, Compound No. 9, Compound No. 10, Compound No. 11 and Compound No. 12 being derived respectively, from TA 1618 + 2 E.O., TA 1618 + 10 E.O., TA 1618 + 15 E.O., Alfol 18 + 2 E.O., Alfol 18 + 10 E.O. and Alfol 18 + 15 E.O.

Each of the above Compounds No. 7 through 12 were oxidized to the corresponding sulfones according to the procedure described in Example 21. The sulfones derived from Compounds No. 7 through No. 12 were respectively designated as Compounds No. 13, through No. 18. The structure of Compounds No. 7 through No. 18 are shown in Table IX.

TABLE IX

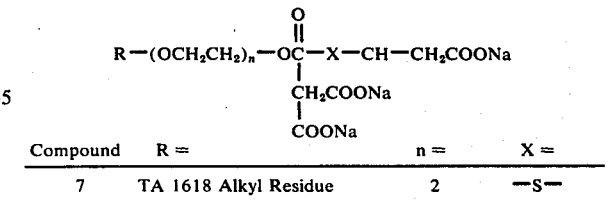

| Compound | R = | n = | X = |
|---|---|---|---|
| 7 | TA 1618 Alkyl Residue | 2 | —S— |

TABLE IX-continued

R—(OCH$_2$CH$_2$)$_n$—OC(=O)—X—CH(CH$_2$COONa)—CH$_2$COONa, with CH$_2$COONa and COONa substituents

| Compound | R = | n = | X = |
|---|---|---|---|
| 8 | TA 1618 Alkyl Residue | 10 | —S— |
| 9 | TA 1618 Alkyl Residue | 15 | —S— |
| 10 | C$_{18}$H$_{37}$ | 2 | —S— |
| 11 | C$_{18}$H$_{37}$ | 10 | —S— |
| 12 | C$_{18}$H$_{37}$ | 15 | —S— |
| 13 | TA 1618 Alkyl Residue | 2 | —SO$_2$— |
| 14 | TA 1618 Alkyl Residue | 10 | —SO$_2$— |
| 15 | TA 1618 Alkyl Residue | 15 | —SO$_2$— |
| 16 | C$_{18}$H$_{37}$ | 2 | —SO$_2$— |
| 17 | C$_{18}$H$_{37}$ | 10 | —SO$_2$— |
| 18 | C$_{18}$H$_{37}$ | 15 | —SO$_2$— |

Compounds 7 through 18 exhibit good detergent-building properties and do not cause build-up on fabric.

What is claimed is:

1. A compound of the formula

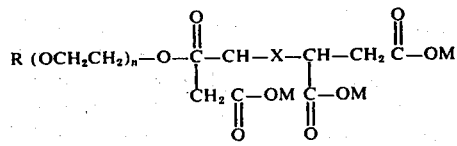

wherein R is a hydrocarbon having from 12 to 22 carbon atoms, X is sulfur, sulfinyl or sulfonyl, M is hydrogen, a monovalent metal, ammonium or substituted ammonium and n is an integer ranging from 2 to 15.

2. A compound according to claim 1 in which R is alkyl or alkenyl.

3. A compound according to claim 2 in which R is a straight chain radical.

4. A compound according to claim 2 in which X is sulfur.

5. A compound according to claim 4 in which n is an integer ranging from 3 to 7.

6. A compound according to claim 4 in which M is hydrogen or sodium.

7. A detergent composition consisting essentially of
   1. an organic water soluble detergent surfactant selected from the group consisting of anionic, nonionic, zwitterionic, and ampholytic detergent surfactants, and mixtures thereof; and
   2. a builder compound of the formula

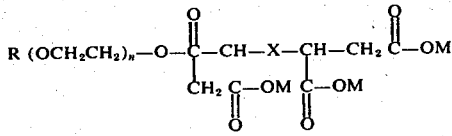

wherein R is a hydrocarbon radical having from 12 to 22 carbon atoms, X is sulfur, sulfinyl, or sulfonyl, M is hydrogen, a monovalent metal, ammonium or substituted ammonium and n is an integer ranging from 2 to 15.

8. A composition according to claim 7 in which the ratio of the builder to the detergent surfactant is in the range of from about 1:5 to about 10:1 by weight.

9. A composition according to claim 8 in which the ratio of the builder to the detergent surfactant is from about 1:2 to about 5:1 by weight.

10. A composition according to claim 7 in which R is alkyl or alkenyl.

11. A composition according to claim 10 in which R is a straight chain radical.

12. A composition according to claim 10 in which X is sulfur.

13. A composition according to claim 10 in which X is sulfonyl.

14. A composition according to claim 12 in which n is an integer ranging from 3 to 7.

15. A composition according to claim 12 in which M is hydrogen or sodium.

* * * * *

UNITED STATES PATENT OFFICE
CERTIFICATE OF CORRECTION

Patent No. 3,976,586   Dated August 24, 1976

Inventor(s) Paritosh M. Chakrabarti

It is certified that error appears in the above-identified patent and that said Letters Patent are hereby corrected as shown below:

The formula appearing in the abstract and the summary of the invention and claims 1 and 7 should appear as follows:

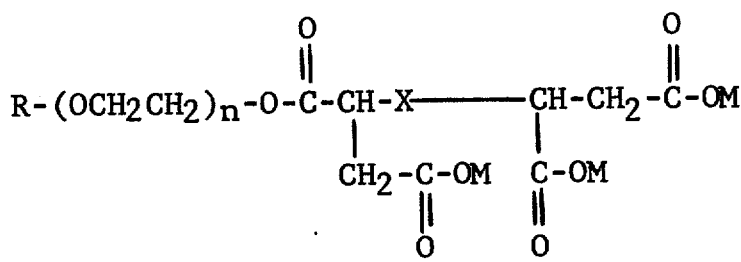

The formula appearing in Table 9 (both occurrences) should appear as follows:

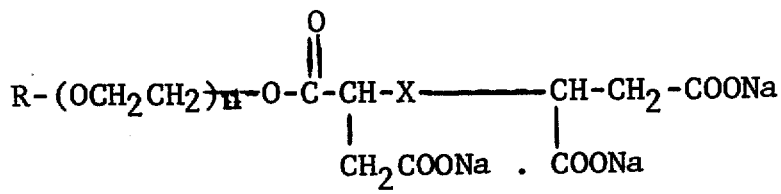

Signed and Sealed this

Tenth Day of November 19;

[SEAL]

Attest:

Attesting Officer

GERALD J. MOSSINGHOFF

Commissioner of Patents and Trademarks